United States Patent [19]

Aine

[11] 4,051,372

[45] Sept. 27, 1977

[54] INFRARED OPTOACOUSTIC GAS ANALYZER HAVING AN IMPROVED GAS INLET SYSTEM

[76] Inventor: Harry E. Aine, 1804 Stierlin Road, Mountain View, Calif. 94040

[21] Appl. No.: 643,179

[22] Filed: Dec. 22, 1975

[51] Int. Cl.² .................. B01D 53/22; G01J 1/00; G01J 3/42; G01V 9/00

[52] U.S. Cl. .................. 250/343; 23/230 EP; 55/158; 250/255; 356/51

[58] Field of Search .............. 250/343, 344, 345, 346, 250/253, 255; 55/158; 23/230, 3, 230 EP; 356/51

[56] References Cited

U.S. PATENT DOCUMENTS

| | | | |
|---|---|---|---|
| 2,165,214 | 7/1939 | Blau et al. | 23/230 EP |
| 3,429,105 | 2/1969 | Llewellyn et al. | 55/158 |
| 3,734,489 | 5/1973 | Milly | 23/230 EP |
| 3,751,880 | 8/1973 | Holm | 55/158 |
| 3,811,319 | 5/1974 | Arnold | 55/158 |
| 3,862,576 | 1/1975 | Pogorski | 23/230 EP |
| 3,893,771 | 7/1975 | Bell | 250/345 |
| 3,911,276 | 10/1975 | Bell | 250/343 |
| 3,926,561 | 12/1975 | Lucero | 55/158 |

Primary Examiner—Alfred E. Smith
Assistant Examiner—T. N. Grigsby
Attorney, Agent, or Firm—Lowhurst & Aine

[57] ABSTRACT

The optoacoustic detector cell of an infrared laser optoacoustic spectrometer is interfaced to a source of gas under analysis, such as the atmosphere, by means of a relatively large area membrane separator. Gas to be analyzed is passed through the membrane separator, compressed by a compressor and then fed at a pressure of between 10 and 1000 torr into the optoacoustic detector cell of the infrared spectrometer for analysis therein. A method of tracing is disclosed wherein deuterium is incorporated into a system to be traced. The deuterium diffuses out of the body in extremely minute quantities which are then inducted into the optoacoustic detector cell of an infrared laser optoacoustic spectrometer via a palladium membrane separator and reactor, whereby an extremely sensitive detection or tracing system is obtained. Also a method of petroleum exploration is disclosed wherein trace quantities of hydrocarbon gases escaping from underground petroleum deposits are detected as a function of position over the area to be explored.

21 Claims, 6 Drawing Figures

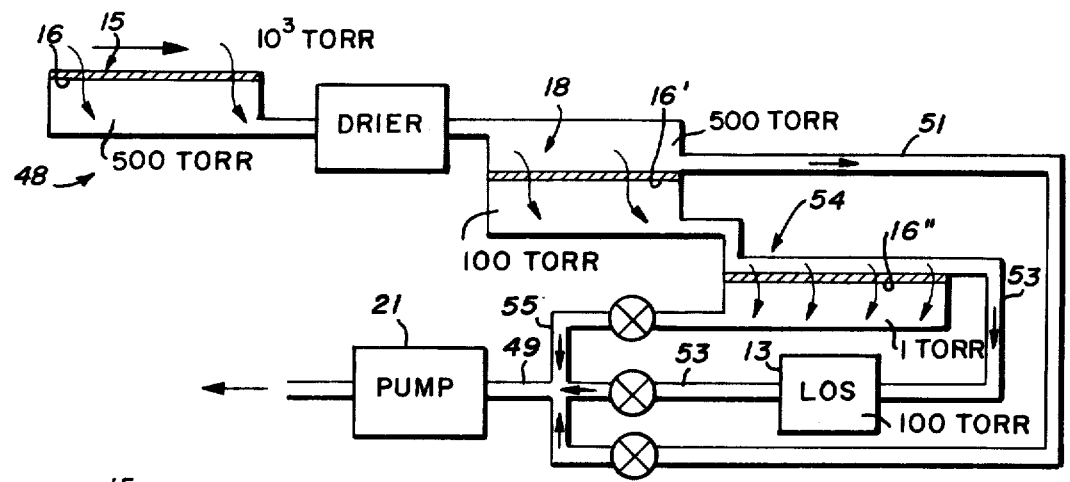
Fig_3
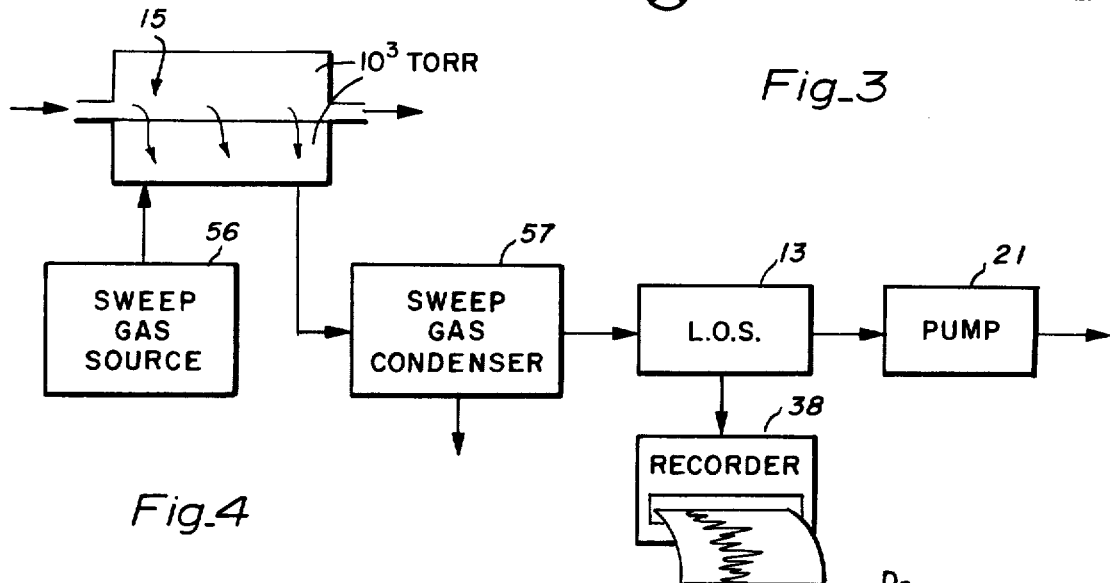
Fig_4
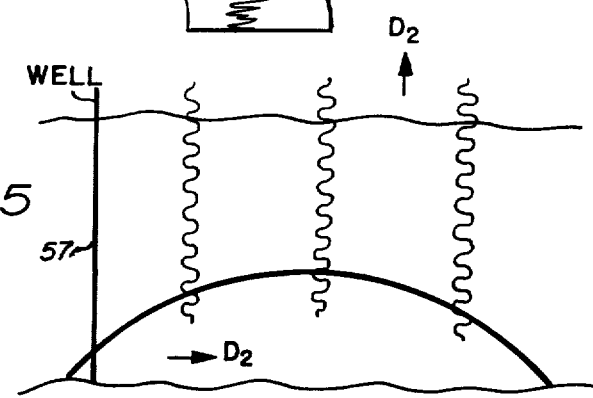
Fig_5
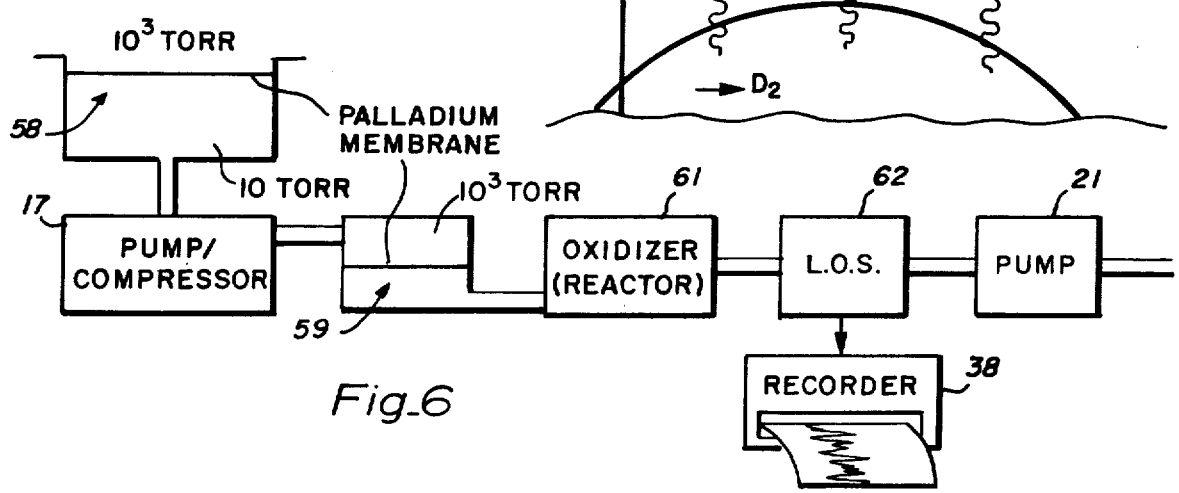
Fig_6

INFRARED OPTOACOUSTIC GAS ANALYZER HAVING AN IMPROVED GAS INLET SYSTEM

BACKGROUND OF THE INVENTION

The present invention relates in general to infrared gas analyzers and more particularly to an improved inlet system for such an analyzer, such inlet system utilizing one or more diffusion membrane stages, preferably combined with one or more compression stages, for greatly increasing the detection sensitivity of the infrared detector as regards certain trace quantities of materials of interest.

DESCRIPTION OF THE PRIOR ART

Heretofore, one or more membrane separator stages have been employed for interfacing a mass spectrometer gas analyzer, operating as a pressure in the range of $10^{-5}$ torr to atmospheric pressure or to other sources of gas to be analyzed, such as a gas chromatograph column operating essentially at atmospheric pressure. Such a system is disclosed in one or more of the following patents: U.S. Pat. Nos. 3,455,092; 3,429,105; 3,398,505; 3,811,319; 3,494,174; 3,638,401; 3,421,292; 3,772,909; British Pat. No. 1,317,912 and Canadian Pat. No. 934,646.

In these prior systems, the gaseous component of the mixture being analyzed is preferentially passed through one or more stages of a membrane separator, each stage being operated at a successively lower pressure so as to reduce the total pressure for the separated gas mixture from atmospheric pressure to a pressure of approximately $10^{-5}$ to $10^{-7}$ torr. In the process, the density of the gaseous constituents of interest are reduced from their respective densities at atmospheric pressure to a much lower density in the ionizer of the mass spectrometer.

This prior art gas inlet system, which is suitable for a mass spectrometer, is totally unsuited for use with an infrared laser optoacoustic spectrometer wherein the optoacoustic detector cell is preferably operated in a pressure regime of 1000 to 50 torr. Also, the detectable quantities of the gaseous constituent of interest, in micrograms within the detector cell, must be several orders of magnitude higher for the laser optoacoustic spectrometer as contrasted with the detectable quantities in a mass spectrometer. However, the mass spectrometer has the disadvantage that the molecules of interest, particularly large hydrocarbons, are fragmented in the ionization process and reconstruction of the detected signals into specific materials is quite difficult.

Accordingly, it is desired to provide a gas inlet system for an infrared laser optoacoustic spectrometer of a type which will discriminate against certain unwanted materials, such as water vapor, permanent gases and light hydrocarbons while passing substantial quantities of the heavier hydrocarbon gaseous constituent of interest to the detector in the absolute pressure range of 10 to 1000 torr. The gas inlet system preferably increases the density of the constituent of interest in the detector cell.

SUMMARY OF THE PRESENT INVENTION

The principal object of the present invention is the provision of an improved gas inlet system for use with an infrared optoacoustic spectrometer.

In one feature of the present invention, the gas constituent of interest is diffused preferentially through a membrane separator and thence into the optoacoustic detector cell of an infrared optoacoustic gas analyzer in the total pressure regime in excess of 10 torr.

In another feature of the present invention, a compressor stage is provided upstream of the detector cell and preferably interposed between the membrane separator and the optoacoustic detector cell for increasing the density of the gaseous constituent of interest in the detector cell.

In another feature of the present invention, a sweep gas is utilized for sweeping the downstream side of the membrane separator, such sweep gas being condensed for separation thereof from the gaseous constituent of interest which is thence fed into the optoacoustic detector cell.

In another feature of the present invention, a tracing system is employed wherein deuterium is incorporated into the body to be traced. The deuterium diffuses from the body and is inducted into the optoacoustic cell of an optoacoustic detector via the intermediary of a palladium membrane separator, whereby an extremely sensitive tracing system is obtained.

Other features and advantages of the present invention will become apparent upon a perusal of the following specification taken in connection with the accompanying drawings wherein:

BRIEF DESCRIPTION OF THE DRAWINGS

FIG. 3 is a schematic diagram, partly in block diagram form, of an alternative embodiment to that of FIG. 2;

FIG. 4 is a schematic diagram, partly in block diagram form, of an alternative embodiment to that of FIG. 3;

FIG. 5 is a schematic line diagram depicting a tracing system incorporating features of the present invention; and FIG. 6 is a schematic diagram, partly in block diagram form, of the laser optoacoustic spectrometer detector useful in the tracing method of FIG. 5.

DESCRIPTION OF THE PREFERRED EMBODIMENTS

Figure 1:
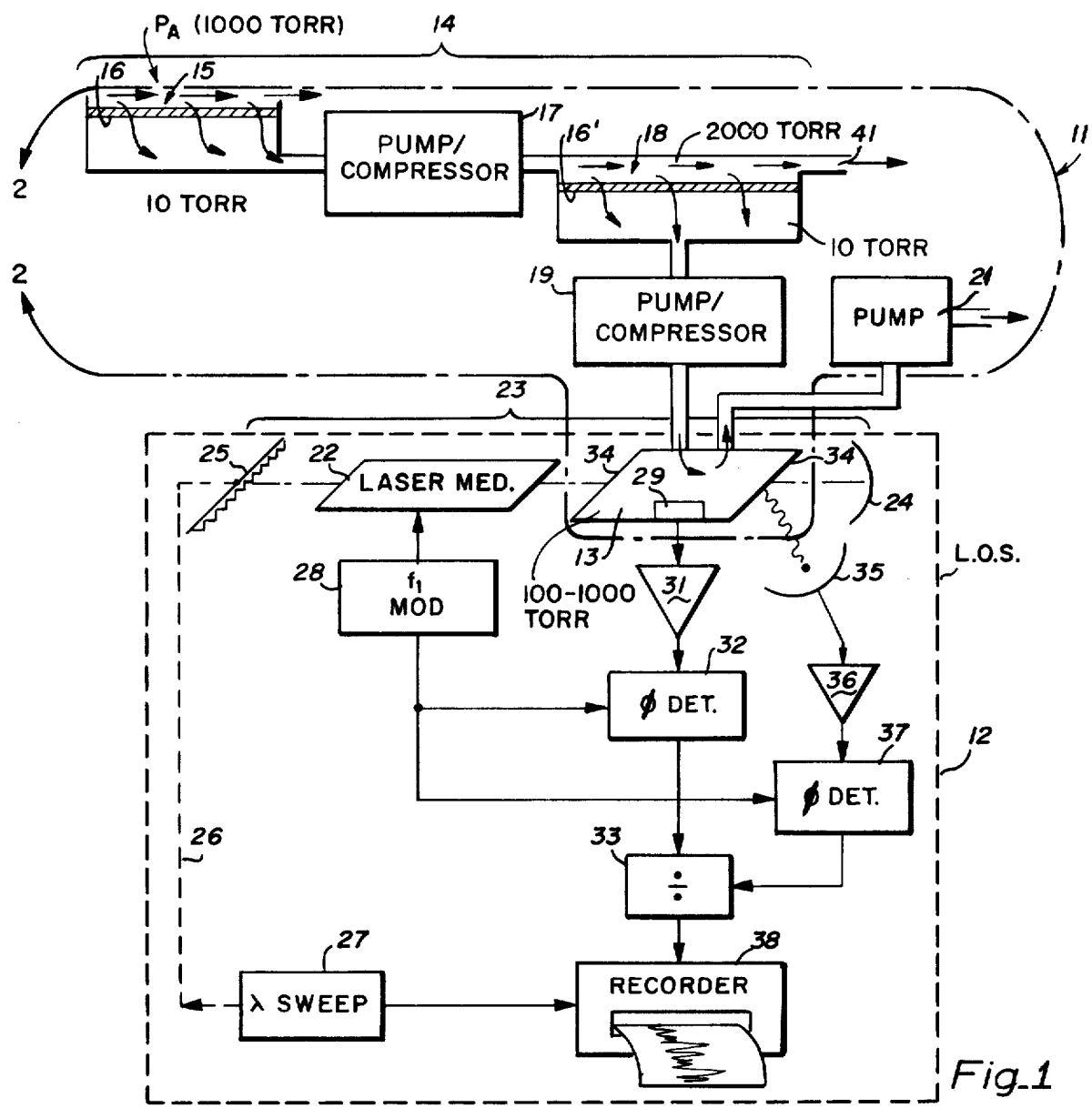
FIG. 1 is a schematic diagram, partly in block diagram form, of a laser optoacoustic spectrometer system incorporating features of the present invention.

Referring now to FIG. 1, there is shown an infrared laser optoacoustic gas analyzer system 11 incorporating features of the present invention. The gas analyzer system 11 includes an infrared laser optoacoustic spectrometer 12 having an optoacoustic detector call 13 coupled in gas communication with a source of gas to be analyzed, such as the atmosphere, via the intermediary of a gas inlet system 14. The gas inlet system 14 includes a first membrane separator stage 15 wherein the gas mixture to be analyzed is fed across the outer surface of a first membrane 16, as of 1 to 5 mil thick polysiloxane polymer having an area of, for example, 1000 square centimeters supported on a porous structure.

Suitable membrane materials are preferably selected from the group consisting of polymers and stationary liquid phases. Stationary liquid phases are those liquid materials employed in chromatographic columns to partition materials to be separated. Comprehensive lists of such materials can be found in numerous publications, one being *Gas Chromatography* by Ernest Bayer, published by Elsevier Publishing Co., New York, 1961, Tables 2, 13 and 14. Other types of suitable diffusion membranes include micropore structures such as that described in U.S. Pat. No. 3,651,618.

Suitable large area support structures include porous wall small diameter hollow tubes of the type disclosed in U.S. Pat. No. 3,339,341, which pass through a chamber and which are coated with the membrane mixture. The gas to be separated is fed through the chamber or tubes, whereas the vacuum is drawn on the tubes or chamber, respectively. As an alternative, the membrane material is coated into a porous hemispherically shaped member as of porous stainless steel.

The membrane 16 is characterized by having a conductance for the gas of interest which is preferably much higher than the conductance of the membrane to other gases which it is desired to separate or exclude from the optoacoustic detector cell 13. Gas is passed through the membrane 16 by the process of diffusion. A vacuum pump/compressor has its input connected to the downstream side of the membrane 16 for drawing a vacuum on the downstream side of the membrane. A suitable vacuum is 10 torr. The gases collected at the intake to the pump 17 are pumped and compressed by a compressor stage to a pressure slightly above atmosphere such as 2000 torr and passed over the input section of a second membrane separator 18.

A second pump and compressor 19 draws a vacuum as of 10 torr on the downstream side of the second membrane separator 18. Pressure at the output of the second compressor 19 is preferably in the range of 100 to 1000 torr and is thence fed through the detector cell for optoacoustic detection of the gaseous constituents of interest therein.

A vacuum pump 21 pulls the sample gases through the detector cell 13 and exhausts them to the atmosphere. Although a simple continuous flow gas inlet system is shown for the laser optoacoustic spectrometer 12, this is not a requirement and if desired an intermittent flow and valving system may be employed as disclosed in an article titled "Laser Optoacoustic Spectroscopy — A New Technique of Gas Analysis" appearing in *Analytical Chemistry*, Vol. 46, No. 2, of February 1974, pages 240a-244a at page 240a.

The laser optoacoustic spectrometer 12 includes a laser tube 22 for containing therein a suitable infrared gas laser gain medium, such as carbon monoxide or carbon dioxide gas which is excited by a suitable power supply to produce a population inversion of the lasing energy transitions of the gas in the band of infrared wavelengths from 0.1 to 20 microns. The laser tube 22 and the optoacoustic cell 13 are placed within an optical cavity 23 having a resonant wavelength at the wavelengh of the predetermined one of the laser lines. The optical cavity 23 is defined by the space between a mirror 24 and a grating 25. The grating 25 is rotatable by means of a mechanical linkage 26 coupled to the output of a wavelength sweeper 27 for shifting the operating wavelength of the laser from one to another over a number of different wavelengths of interest.

The laser is intensity modulated by means of a modulator 28 at a convenient low frequency as of 10 Hertz, such modulator 28 serving to intensity modulate the laser by modulating the power applied to excite the laser gain medium.

The intensity modulated laser beam passes through the optoacoustic detector cell 13 which contains a microphone or pressure sensitive detector 29. When the wavelength of the infrared laser beam energy corresponds to an absorption line of the sample gas under analysis in the cell 13, energy is absorbed by the sample gas constituent producing heating of the sample gas. The heating produces a pressure rise or an acoustic wave in the optoacoustic detector cell 13 which is detected by the pressure sensitive device 29.

The detected signal, at the beam modulation frequency or at a harmonic thereof, is fed via an amplifier 31 to one input of a phase sensitive detector 32 for detection against a sample of the modulation frequency derived from modulator 28. The phase sensitive detected output of a phase sensitive detector 32 is thence fed to one input of a divider 33 for division by a second phase sensitive detected signal corresponding to the beam power. More specifically, a portion of the infrared beam power is reflected from one of the Brewster angle windows 34 covering opposite ends of the optoacoustic detector cell 13. This reflected energy is picked up by an infrared photodetector 35 and amplified by amplifier 36 and thence phase sensitive detected against a sample of the modulation frequency derived from modulator 28 in a phase sensitive detector 37 to derive an output representative of the beam intensity which is fed to the other input of the divider 33 for comparison with the phase sensitive detected optoacoustic signal.

The output of the divider 33 is an optoacoustic absorption signal normalized to the beam power which is thence fed to one input of a recorder 38 for recording against a sample of the sweep signal derived from the sweep generator 27 to obtain an infrared absorption spectrum of the sample gas under analysis.

In a typical example of the gas analyzer system 11 of FIG. 1, the optoacoustic detector cell 13 would have a volume of approximately 10cc with a measurement time of approximately ten seconds for that volume. The flow rate through the optoacoustic cell 13 is then approximately 1cc per second. The total pressure of the gas in the optoacoustic detector cell 13 is preferably in the range of 1000-100 torr. Assuming the detector cell total pressure is to be 1000 torr, and that the molar concentration of the hydrocarbon species to be measured in the cell 13 is $10^{-9}$ or approximately $10^{-6}$ torr (for a molecular weight of 28), the weight of the sample constituent of interest in 1cc of the air at standard temperature and pressure and at a partial pressure of $10^{-6}$ torr is approximately $10^{-12}$ grams. Accordingly, for a measurement in the detector cell 13 under these conditions, $10^{-12}$ grams per second of the gaseous constituent of interest must pass through the optoacoustic detector cell 13.

The first membrane separator 15 must pass this amount of material per second. Assuming the partial pressure of the hydrocarbon species of interest in the atmosphere is $10^{-9}$ torr, i.e., $10^{-12}$ molar concentration, the area of the first membrane is approximately 1000 square centimeters for a hydrocarbon of interest having conductivity through the first membrane of approximately 1 to 5 cc per square centimeters per second which is typical for 1 to 5 mil thick polysiloxane polymer.

The conductivity for water vapor is approximately 0.003 and for the permanent gases nitrogen and oxygen is approximately 0.001. Thus, it is seen that the hydrocarbons are preferentially diffused through the membrane 16. The first membrane separator stage 15 gives an enrichment of approximately $10^3$ in favor of the hydrocarbon over air.

The second membrane separator 18 is chosen with a membrane area equal to that of the first membrane 16, i.e., approximately 1000 square centimeters. The exhaust conductivity out of exhaust orifice 41 is chosen such that about one-half of the hydrocarbon molecules are exhausted through that orifice 41 and the other half diffused through the second separator 18. This means that the majority of the air molecules between separators 16 and 18 are exhausted through the orifice 41.

The second membrane separator 18 will pass approximately $\frac{1}{2} \times$ ($10^{-6}$ torr cc/seconds) of the hydrocarbon. Second separator membrane 16' will pass one torr cc per second of air. The second pump 19 maintains a pressure differential across the second membrane separator 18 of 2000 torr. The partial pressure ratio of the gas constituent of interest, i.e., the hydrocarbon to that of air on the downstream side of the second membrane separator 18 is approximately $\frac{1}{2} \times 10^{-6}$. This is an improvement by a factor of $5 \times 10^5$ over the original ratio of partial pressures. The volume of gas and air is then compressed by the pump and compressor 19 by a factor of 100 to 1000 to yield a total pressure of 100 to 1000 torr with a partial pressure ratio of $5 \times 10^{-7}$ of the gaseous hydrocarbon constituents of interest inside the optoacoustic cell instead of $10^{-12}$ as encountered in the original mixture of air at atmospheric pressure.

Figure 2:
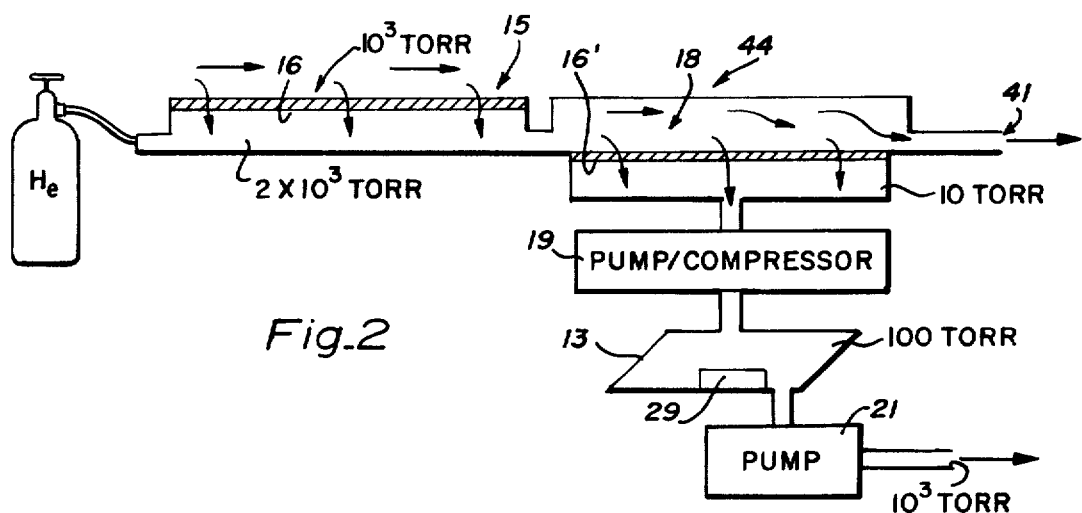
FIG. 2 is a schematic circuit diagram, partly in block diagram form, of an alternative embodiment of a portion of the structure of FIG. 1 delineated by line 2—2.

Referring now to FIG. 2 there is shown an alternative embodiment of a gas inlet system 44 incorporating features of the present invention. More particularly, a first membrane separator 15 has a purified sweep gas, such as purified helium, at slightly above atmospheric pressure fed across the downstream side thereof so that the gaseous constituent of interest diffuses through the membrane 16 into the carrier or sweep gas stream. The gas diffuses across the membrane because there is a substantial partial pressure differential between the partial pressure of the hydrocarbon gaseous constituent of interest in the air on the upstream side of the membrane and in the helium on the downstream side of the membrane.

The sweep gas carries the constituent of interest across the membrane 16' of a second membrane separator 18. The pump and compressor 19 draws a partial vacuum on the downstream side of the second membrane separator 18. The pump and compressor increases the total pressure of the gas mixture in passing through the second membrane to a total pressure within the range of 100 to 1000 torr which is thence fed to the optoacoustic detector cell 13 and thence to the atmosphere via a second vacuum pump 21. The advantage to the system of FIG. 2 over that of FIG. 1 is that the first pump and compressor 17 has been omitted such that the remaining pump and compressor 19 must pump and compress a much smaller mass of material than that required in the system of FIG. 1.

Referring now to FIG. 3 there is shown an alternative embodiment of the gas inlet system of the present invention. More particularly, gas inlet system 48 of FIG. 3 includes a single pump 21 which via a manifold 49 and line 51 draws a vacuum as to 500 torr on the downstream side of the first membrane separator 15. The flow of gas passing through the first membrane separator 15 passes through a drier, such as a water vapor absorption pump. A suitable pump would include a cannister filled with a desiccant or other absorption material such as zeolite. The dried gaseous mixture is thence fed to a second membrane separator 18 wherein the gaseous constituents of interest are preferentially diffused through the membrane to the downstream side thereof operating at subatmospheric pressure, as of 100 torr. The subatmospheric pressure is drawn on the downstream side of separator 18 via a vacuum line 53 interconnecting the manifold 49 and the separator 18 via the laser optoacoustic detector cell 13.

A third membrane separator 54 is interposed between the second membrane separator 18 and the cell 13. The third membrane separator 54 is arranged for removing hydrocarbons which are heavier than the hydrocarbon of interest from the gas stream fed to the cell 13. For example, the first two membrane separators 15 and 18 serve to preferentially remove certain undesired gaseous constituents, such as the permanent gases, and low weight hydrocarbons such as $CH_4$; whereas the heavier hydrocarbons were retained in the gas flow stream through the two separators. However, the third separator 54 has a vacuum drawn on the downstream side thereof from the manifold 49 via vacuum line 55 and it serves to preferentially remove the higher boiling point hydrocarbons such that the lower boiling point hydrocarbons remain in the flow stream through the optoacoustic cell 13. Pressure regulators 50 are provided on each vacuum line 51, 53 and 54 for regulating the pressure.

In a typical example, the first two membrane separators 15 and 18 would serve to preferentially pass propane and higher hydrocarbons therethrough, whereas the third membrane separator 54 would preferentially remove the hydrocarbons having higher boiling points than propane such that selective detection of propane in the presence of other interfering gaseous species, such as $H_2O$ and $CH_4$, is facilitated. Compressors 17 and 18 may be employed in the embodiment of FIG. 3 to increase the density of the hydrocarbon constituent of interest in the manner as previously described with regard to FIGS. 1 and 2. Referring now to FIG. 4 there is shown an alternative gas inlet system of the present invention. More particularly, gas to be analyzed is fed through a first membrane separator 15. A condensible sweep gas, such as steam, ammonia or freon, supplied from a source 56 through the downstream chamber of the separator into a sweep gas condenser 57. In the sweep gas condenser, sweep gas is liquified or solidified and separated from the gases of interest which are passed through the first stage of the membrane separator 15. The separator gas of interest is then adjusted in absolute pressure by means of a compressor or by introduction of a suitable pressure and flow of carrier gas, and fed through the LOS cell 13 to the atmosphere via pump 21. The output of the optoacoustic spectrometer is recorded on the recorder 38.

Referring now to FIG. 5, there is shown a method for tracing and more particularly, a method for determining the boundaries of a porous formation. More particularly, deuterium is injected into the formation via a well 57. The deuterium diffuses rapidly through the formation and also through the overburden to the surface. At the surface, the detection system of the type shown in FIG. 6 is employed for detecting minute quantities of the deuterium.

A palladium membrane separator 58 causes the deuterium to preferentially diffuse through the membrane separator 58 to the downstream side thereof operated at a pressure as of 10 torr via a pump and compressor combination 17. The palladium membrane preferentially passes the deuterium which is then compressed to atmospheric pressure and fed through a second palladium membrane separator 59. The deuterium component of the output of the second membrane separator 59 is then oxidized or otherwise reacted to produce compounds such as $D_2O$, $CD_4$ or some other compound having an absorption line in the infrared.

The reaction product is thence fed through the optoacoustic cell of a laser optoacoustic spectrometer 62. The deuterium line will be slightly shifted from the corresponding hydrogen compound such as water vapor. The shifted deuterium absorption line is detected by the laser optoacoustic spectrometer (LOS) and the results thereof recorded on recorder 38. The optoacoustic detector cell 13 is exhausted to the atmosphere via the pump 21 in the manner as previously described with regard to the other embodiments.

The gas detection system of the present invention is particularly useful for petroleum exploration by detecting minute quantities, i.e. parts per million or billion or more, of hydrocarbon gases, such as ethane or propane or both, diffusing into the atmosphere through the overburden from underground petroleum deposits. The gas detector system of FIGS. 1–6 is carried over the region to be explored as by aircraft, land vehicle or ship and the concentration of the gaseous component or ratios thereof are detected as a function of position over the area to be explored, whereby plumes of such gases are detected to permit pin pointing of the underground petroleum deposits.

What is claimed is:

1. In an inlet system for introducing gaseous material from a source into the optoacoustic region of an infrared optoacoustic gas analyzer:
   membrane separator means having a membrane of the type which has a higher value of diffusion conductance to a first gaseous component than to a second gaseous component of the gas mixture to be analyzed and is dimensioned and arranged for diffusion therethrough of amounts of said first gaseous component at a sufficient rate for detection in the optoacoustic detector region;
   means for diffusing a portion of said gas mixture through said membrane of said membrane separator means so as to conduct said first gaseous component through said membrane with a higher value of conductance than that of said second gaseous component; and
   means for operation at a total pressure in excess of 10 torr and for conducting said separated first gaseous component of said gas mixture at a total pressure in excess of 10 torr into the optoacoustic detection region of optoacoustic gas analyzer.

2. The apparatus of claim 1 wherein said first gas component of said gas mixture to be analyzed has a first value of partial pressure in said mixture to be analyzed, and means for increasing the partial pressure of said first gaseous component of said mixture and for feeding said first gas component at a partial pressure in excess of said first value into said optoacoustic detection region of said optoacoustic gas analyzer.

3. The apparatus of claim 2 wherein said means for increasing the partial pressure of said first gas component of said gas mixture is disposed so as to receive said gas mixture after having passed through said separator means and for thereafter increasing said partial pressure of said first gas component in said mixture prior to passage thereof into said optoacoustic detection region at said total pressure in excess of 10 torr.

4. The apparatus of claim 2 wherein said gas mixture to be analyzed is air having a trace quantity of said first gas component therein.

5. In a gas analyzer system:
   infrared optoacoustic gas analyzer means having an optoacoustic detector cell for containing a volume of gas to be analyzed at a pressure in excess of 10 torr and into which volume of gas modulated infrared radient energy is directed to produce modulated absorption of infrared energy by said gas under analysis resulting in producing a modulated pressure in said detector cell which is detected by a pressure sensitive detector;
   gas inlet system means for introducing gaseous material from a source into said optoacoustic detector region of said infrared optoacoustic gas analyzer means;
   said inlet system means including membrane separator means having a membrane of the type which has a higher value of diffusion conductance to a first gaseous component than to a second gaseous component of a gas mixture to be analyzed, said membrane separator means being dimensioned and arranged for diffusion therethrough of amounts of said first gaseous component at a sufficient rate for detection in the optoacoustic cell;
   means for diffusing a portion of said gas mixture through said membrane of said membrane separator means so as to conduct said first gaseous component through said membrane with a higher value of conductance than that of said second gaseous component; and
   means for conducting said separated first gaseous component of said gas mixture at a total pressure in excess of 10 torr into the optoacoustic detection region of the optoacoustic gas analyzer.

6. The apparatus of claim 5 wherein said first gas component of said gas mixture to be analyzed has a first value of density in said mixture to be analyzed and including means for increasing the density of said first gaseous component of said mixture and for feeding said first gas component at said increased density in excess of said first value of density into said optoacoustic detection region of said optoacoustic gas analyzer means.

7. The apparatus of claim 6 wherein said means for increasing the density of said first gas component of said gas mixture is disposed so as to receive said gas mixture after having passed through said separator means and for thereafter increasing said density of said first gas component in said mixture prior to passage thereof into said optoacoustic detector region at said total pressure in excess of 10 torr.

8. The apparatus of claim 7 wherein said gas mixture to be analyzed is air having a trace quantity of said first gas component therein.

9. The apparatus of claim 7 wherein said means for increasing the density of said first gas component comprises compressor means for compressing the volume of said first gas component.

10. In a method for introducing gaseous material from a source into the optoacoustic detector region of an infrared optoacoustic gas analyzer, the steps of:
    feeding the gas mixture to be analyzed through a membrane separator having a membrane of the type which has a higher value of diffusion conductance to a first gas component of the mixture than to a second gas component of the gas mixture to be analyzed and which is dimensioned and arranged for diffusion therethrough of amounts of said first gaseous component at a sufficient rate for detection in the optoacoustic detector region so as to conduct said first gaseous component through said membrane with a higher value of conductance than that of said second gaseous component; and conducting said separated first gaseous component of said gas mixture at a total pressure in excess of 10 torr into the optoacoustic detector region of the optoacoustic gas analyzer.

11. The method of claim 10 wherein said first gas component of said gas mixture to be analyzed has a first value of density in said gas mixture to be analyzed and including the step of increasing the density of said first gas component in said gas mixture after passage thereof through said separator means and prior to feeding of said first gaseous component into the detector region of said optoacoustic gas analyzer.

12. The method of claim 11 wherein the step of increasing the density of the first gas component of said gas mixture comprises the step of compressing the gas mixture after passage thereof through said separator means and prior to passage thereof into said optoacoustic detector region of said optoacoustic detector.

13. The method of claim 10 wherein said gas mixture to be analyzed is air having a trace quantity of said first gas component therein.

14. In a method for analyzing a gas mixture having first and second gaseous components therein, the steps of:

directing modulated infrared radiant energy through an optoacoustic detector cell containing the gas mixture to be analyzed for producing a modulated absorption of infrared energy by the gas resulting in producing a modulated pressure wave which is detected by a pressure sensitive detector in gas communication with the cell;

passing the gas to be analyzed from a source into the detector cell via the intermediary of a membrane separator of the type which has a higher value of diffusion conductance to a first gaseous component of the mixture than to a second gaseous component of the mixture so as to conduct said first gaseous component through said membrane separator with a higher value of conductance than that of said second gaseous component; and passing said separated first gaseous component of said gas mixture at a total pressure in excess of 10 torr into the optoacoustic detector region of the optoacoustic gas analyzer.

15. The method of claim 14 wherein said first gas component has a density of a first value in said gas mixture to be analyzed and including the step of increasing the density of said first gaseous component of said gas mixture and feeding said first gas component at a value of density in excess of said first value into the optoacoustic detector cell of said optoacoustic gas analyzer.

16. The method of claim 15 wherein the step of increasing the density of said first gaseous component of said gas mixture comprises the step of compressing said gas mixture so as to increase the density of said first gaseous component of said gas mixture.

17. The method of claim 14 wherein said gas mixture to be analyzed is air having a trace quantity of said first gas component therein.

18. The method of claim 14 including the step of drawing off of said separated gas mixture gaseous components having higher boiling points than said first gas component by directing said higher boiling point gaseous components through a diffusion membrane having a higher value of conductance for said higher boiling point gaseous components than the value of conductance for that of said first gaseous component.

19. In a method for detecting the presence of a body, the steps of:

incorporating deuterium in the body to be detected;

detecting deuterium escaping from the body by passing the escaping deuterium through a membrane separator;

reacting the deuterium having passed through the separator to produce an infrared absorption reaction product compound;

passing the reaction product compound into the optoacoustic detector cell of infrared optoacoustic detector for detection thereof.

20. In a method of petroleum exploration, the steps of:

traversing an area to be explored with an infrared laser optoacoustic gas detector and detecting at least one gaseous component in the atmosphere as a function of position in the area to be explored and such gaseous component being associated with buried deposits of petroleum, such detected gaseous component having diffused from the region of the buried deposit through the overburden and escaped into the atmosphere, and wherein the step of detecting the gaseous component in the atmosphere includes:

feeding a sample of the gaseous atmosphere to be analyzed through a membrane separator having a membrane of the type which has a higher value of diffusion conductance to a first gaseous component of the mixture than to a second gaseous component of the gas mixture to be analyzed so as to conduct said first gaseous component through said membrane with a higher value of conductance than that of said second gaseous component; and conducting said separated first gaseous component of said gas mixture at a total pressure in excess of 10 torr into the optoacoustic detector region of the gas detector.

21. The method of claim 20 wherein the gaseous component to be detected is selected from the class consisting of propane and ethane.

* * * * *